(12) United States Patent
Li et al.

(10) Patent No.: US 10,420,291 B2
(45) Date of Patent: Sep. 24, 2019

(54) FOLIAGE BLOCKING AGENT FOR PRECISE REGULATION OF EXPRESSION OF CADMIUM ABSORPTION AND TRANSPORTATION-RELATED GENE IN RICE AND APPLICATION THEREOF

(71) Applicant: Guangdong Institute of Eco-Environmental Science & Technology, Guangzhou (CN)

(72) Inventors: Fangbai Li, Guangzhou (CN); Chuanping Liu, Guangzhou (CN); Jianghu Cui, Guangzhou (CN)

(73) Assignee: Guangdong Institute of Eco-Environmental Science & Technology, Guangdong Province (CN)

(*) Notice: Subject to any disclaimer, the term of this patent is extended or adjusted under 35 U.S.C. 154(b) by 23 days.

(21) Appl. No.: 15/861,123

(22) Filed: Jan. 3, 2018

(65) Prior Publication Data
US 2018/0153109 A1 Jun. 7, 2018

Related U.S. Application Data

(63) Continuation of application No. PCT/CN2016/079111, filed on Apr. 12, 2016.

(30) Foreign Application Priority Data

Mar. 2, 2016 (CN) .......................... 2016 1 0119054

(51) Int. Cl.
| | | |
|---|---|---|
| *A01N 25/04* | (2006.01) | |
| *A01N 43/08* | (2006.01) | |
| *A01N 59/02* | (2006.01) | |
| *A01G 22/22* | (2018.01) | |
| *A01G 7/06* | (2006.01) | |
| *C05D 9/00* | (2006.01) | |

(52) U.S. Cl.
CPC ............. *A01G 22/22* (2018.02); *A01G 7/06* (2013.01); *A01N 25/04* (2013.01); *A01N 43/08* (2013.01); *A01N 59/02* (2013.01); *C05D 9/00* (2013.01)

(58) Field of Classification Search
None
See application file for complete search history.

(56) References Cited

U.S. PATENT DOCUMENTS 9,919,978 B2 * 3/2018 Liu .................... A01N 59/02

FOREIGN PATENT DOCUMENTS

| | | | |
|---|---|---|---|
| CN | 1789113 A | * | 6/2006 |
| CN | 1789113 A | * | 6/2006 |
| CN | 1789113 A | | 6/2006 |
| CN | 1907029 A | | 2/2007 |
| CN | 101830735 A | | 9/2010 |
| CN | 102744030 A | | 10/2012 |
| CN | 101851133 B | | 2/2013 |
| CN | 103789114 A | | 5/2014 |
| CN | 105075763 A | | 11/2015 |
| EP | 298368 | * | 1/1989 |
| EP | 0369545 B1 | | 8/1992 |
| WO | WO-2015096533 A1 | * | 7/2015 ............. A01N 59/02 |

OTHER PUBLICATIONS

Zhang et al., Synthesis, characterization, and controlled release of selenium nanoparticles stabilized by chitosan of different molecular weights, Carbohydrate Polymers 134 (2015) 158-166. (Year: 2015).*
Jia et al., Construction of selenium nanoparticles/b-glucan composites for enhancement of the antitumor activity, Carbohydrate Polymers (2015), vol. 117, pp. 434-442 (Year: 2015).*
International Search Report for WO 2017/147980A1, dated Nov. 30, 2016.
Xu Xianghua et al., Foliar application of selenium-silicon sol reduced arsenic accumulation in rice [J]: Ecology and Environmental Sciences, 2014, 23(6); 1064-1069.

* cited by examiner

*Primary Examiner* — Alton N Pryor
(74) *Attorney, Agent, or Firm* — Hahn Loeser & Parks LLP (57) ABSTRACT

The present invention relates to the field of environmental protection, and in particular to a leaf surface barrier for accurately controlling cadmium absorption and transport related gene expression in rice, and an application thereof. The present invention comprises: reducing a raw material, i.e., selenious acid or selenite, by using ascorbic acid to generate a nanogel, and then emulsifying the nanogel for peptization to obtain a leaf surface barrier for accurately controlling cadmium absorption and transport related gene expression in rice; and then mixing the leaf surface barrier with a silica sol to obtain a composite selenium and silica sol leaf surface barrier. The present invention also provides a leaf surface barricading method for accurately controlling cadmium absorption and transport related gene expression in rice. By applying the leaf surface barrier, the silica sol or the composite selenium and silica sol leaf surface barrier having a particular atomization degree and a particular concentration by means of foliar spray during a particular growth period of rice and within a particular time, the cadmium accumulation in rice can be effectively reduced. Applying the present invention to a moderately or lightly polluted field can enable cadmium content in rice to satisfy the food hygiene standards, and therefore is significant for achieving the safe use of the large area of field polluted by heavy metal cadmium in China.

7 Claims, 3 Drawing Sheets

Specification includes a Sequence Listing.

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: primer OsNramp5-F

<400> SEQUENCE: 1
tgagctgctc tgggtgattc                                              20

<210> SEQ ID NO 2
<211> LENGTH: 20
<212> TYPE: DNA
<213> ORGANISM: Artificial Sequence
<220> FEATURE:
<223> OTHER INFORMATION: primer OsNramp5-R

<400> SEQUENCE: 2
tgccagcagc cataggaaaa                                              20

<210> SEQ ID NO 3
<211> LENGTH: 20
<212> TYPE: DNA
<213> ORGANISM: Artificial Sequence
<220> FEATURE:
<223> OTHER INFORMATION: Primer OsLCT1-F

<400> SEQUENCE: 3
tggcgatctt tggaggcttt                                              20

<210> SEQ ID NO 4
<211> LENGTH: 20
<212> TYPE: DNA
<213> ORGANISM: Artificial Sequence
<220> FEATURE:
<223> OTHER INFORMATION: Primer OsLCT1-R

<400> SEQUENCE: 4
cgccgaggtc gataagaaca                                              20

<210> SEQ ID NO 5
<211> LENGTH: 20
<212> TYPE: DNA
<213> ORGANISM: Artificial Sequence
<220> FEATURE:
<223> OTHER INFORMATION: Primer OsHMA3-F

```
<400> SEQUENCE: 5
agaacagcag gtcgaagacg                                               20

<210> SEQ ID NO 6
<211> LENGTH: 20
<212> TYPE: DNA
<213> ORGANISM: Artificial Sequence
<220> FEATURE:
<223> OTHER INFORMATION: Primer OsHMA3-R

<400> SEQUENCE: 6
attgctcaag gccatctgct                                               20

<210> SEQ ID NO 7
<211> LENGTH: 21
<212> TYPE: DNA
<213> ORGANISM: Artificial Sequence
<220> FEATURE:
<223> OTHER INFORMATION: Primer OSLsi1-F

<400> SEQUENCE: 7
cggtggatgt gatcggaacc a                                             21

<210> SEQ ID NO 8
<211> LENGTH: 21
<212> TYPE: DNA
<213> ORGANISM: Artificial Sequence
<220> FEATURE:
<223> OTHER INFORMATION: Primer OSLsi1-R

<400> SEQUENCE: 8
cgtcgaactt gttgctcgcc a                                             21

<210> SEQ ID NO 9
<211> LENGTH: 19
<212> TYPE: DNA
<213> ORGANISM: Artificial Sequence
<220> FEATURE:
<223> OTHER INFORMATION: Primer OSLsi2-F

<400> SEQUENCE: 9
atctgggact tcatggccc                                                19

<210> SEQ ID NO 10
<211> LENGTH: 19
<212> TYPE: DNA
<213> ORGANISM: Artificial Sequence
<220> FEATURE:
<223> OTHER INFORMATION: Primer OSLsi2-R

<400> SEQUENCE: 10
acgtttgatg cgaggttgg                                                19
```

FOLIAGE BLOCKING AGENT FOR PRECISE REGULATION OF EXPRESSION OF CADMIUM ABSORPTION AND TRANSPORTATION-RELATED GENE IN RICE AND APPLICATION THEREOF

CROSS-REFERENCE TO RELATED APPLICATIONS

The present application is a continuation of International Application No. PCT/CN2016/079111 filed on Apr. 12, 2016, designating the United States of America and published in Chinese on Sep. 8, 2017, which in turn claims priority to Chinese Application 201610119054.9 filed on Mar. 2, 2016, both of which are hereby incorporated by reference in their entirety.

TECHNICAL FIELD

The present invention relates to the field of environmental protection, particularly to a foliage blocking agent for precise regulation of the expression of the cadmium absorption and transportation-related gene in rice and application thereof.

BACKGROUND ART

As disclosed in "Report on the national general survey of soil contamination" issued in 2014 by Ministry of Environmental Protection of the People's Republic of China and Ministry of Land and Resources of the People's Republic of China, the cadmium contaminated soil area accounts for 7.0% in China, therefore the treatment of the cadmium contamination in soil is a serious environmental problem to be solved in China, wherein the cadmium contamination is particularly prominent in rice field.

The treatment technologies against the cadmium contamination in rice field, are roughly divided into two classes on the basis of the treatment objectives, a remediation technology of removal of the heavy metals in soil, which has an objective for making the soil quality meet the environmental standards, and a contamination control technology, which has an objective for guaranteeing the safety of agricultural products.

At present, it has been confirmed that the cadmium hyper-accumulated plants mainly comprise *Sedum alfredii* Hance, sedum plumbizincicola, *Solanum nigrum* L., *Thlaspi arvense* L., and the like, and the cadmium enriched plants comprise *Amaranthus hypochondriacus* L, and the like. The plant remediation technology requires to occupy farmland and farming time, requires a large investment of funds, therefore it is hard to be applied in a large area. At present, the plant remediation technology is only suitable for dry lands, and there are no reports on application of the same in the flooded rice field yet. In addition, there are no one-to-one correlation between the heavy metal contents in soil and the heavy metal contents in agricultural products, therefore reduction of the heavy metal contents in soil to meet the standard level can not guarantee that the safeties of the agricultural products meet the standard levels.

Obviously, the remediation of the cadmium contamination in rice field is difficult and presents many technical bottlenecks, therefore the removal technique is difficult to solve the cadmium contamination in the regional rice field. It is a practical and feasible technical approach for improving the quality of the agricultural products by reducing the bioavailability of cadmium, preventing the absorption and accumulation of cadmium in rice, particularly inhibiting the transportation of cadmium from the rice leaves to the grains.

A new technical idea for controlling the heavy metal contamination in farmlands is disclosed in Chinese Patent Nos. 200610036994.8, 201010156359.X, 201010156358.5, 201310737996.X, etc.: the composite silica sol is directly sprayed on the surface of the rice leaves, without treating the soil, so as to effectively reduce the heavy metal contents in the agricultural products.

In technical principles, cadmium is a non-essential element in rice, which can compete for the transport proteins for the essential elements or the beneficial elements, such as Si, Zn, Fe, Mn and the like, so as to enter the roots and be transported upward into the grains (Uraguchi & Fujiwara, 2013). The accumulation of cadmium in rice grains mainly involves in four processes: absorption in the root, transportation in the xylem, transportation across the vascular bundles, and migration from the phloem to the grains (Uraguchi & Fujiwara, 2012). At present, some important genes which are related to the cadmium absorption in rice and their expression products, the transport proteins, have been identified. In the process of the cadmium absorption in the rice roots, the iron transport protein produced by the expression of the constitutive gene OsNramp5 can absorb Mn and Fe, and simultaneously efficiently transport cadmium (Sasaki et al., 2012), the zinc iron transport protein produced by the expression of the genes OsZIP1 and OsZIP3 can transport Zn and Fe, and simultaneously transport cadmium (Ramesh et al., 2003), in addition, the iron transport protein produced by the expression of the Fe-deficiency induction gene OsNramp1, OsIRT1 and OsIRT2 can promote the Fe absorption and simultaneously enhance the cadmium absorption (Takahashi et al., 2011; Nakanishi et al., 2006; Lee & An, 2009). In the process of loading in the xylem and upward transportation, the transport protein produced by the expression of gene OsHMA2 can load Zn in the xylem, and simultaneously can load cadmium (Nocito et al, 2011; Takahashi et al., 2012), the transport protein produced by the expression of genes OsHMA3, OsMTP1, OsABCG43/OsPDR5, etc., can transport the elements, such as zinc, cadmium, and the like, into the vacuoles so as to maintain the equilibrium state of the various elements in the cells, and inhibit the transportation thereof into the xylem (Ueno et al., 2010; Miyadate et al., 2011; Menguer et al., 2013; Oda et al., 2011). In the process of the loading in the phloem and the transportation into the grains, mainly the transport proteins such as OsLCT1 and the like, can regulate the transportation of the heavy metal elements, such as manganese, cadmium, etc., from the phloem into the grains (Uraguchi et al., 2011).

On the basis of the above analysis, the absorption and transportation of the non-essential elements, such as cadmium and the like, in the rice body, can typically be achieved by means of the transport proteins for the essential elements having similar structures, such as Fe, Zn, Si, and the like, and at present, the specific transport protein which can solely transport the heavy metal cadmium has not be found yet. Therefore, on the basis of the characteristics that the heavy metal elements compete for the same transport proteins with the essential elements, the application of the exogenous essential elements can prevent the absorption and in vivo transportation of the heavy metal.

In addition, rice is a typical silicon-philic plant, however, up to now, it is uncertain that silicon is the essential element for plant growth, but there are sufficient evidences showing that silicon is necessary for the rice production in stable and high yield. Silicon is present in the juice in the xylem of the plant, mainly in monosilicic acid state [Si(OH)$_4$], with a small proportion of ionic state Si(H$_3$SiO$_4$$^-$). The ionic state of silicon has a slight high proportion in the rice roots, up to 3%~8%, dominantly in Si(OH)$_4$ form; the vast majority of the silicon in the rice body is present in the form of hydrated amorphous silica SiO$_2$.H$_2$O or polysilicic acid, accounts for about 90%~95% of the total silicon content, and a minority thereof is silicic acid, colloidal silicic acid and silicate ions.

The absorption of silicon in rice is a typical active absorption process, and silicon is absorbed in the form of silicic acid in the rice roots, therefore such active transportation makes the silicic acid content in the solution in the rice xylem is many times higher than that in the solution outside the roots. At present, three Si transport genes (OsLsi1, OsLsi2 and OsLsi6) have been successfully cloned from the rice silicon absorption-deficient mutants, wherein the genes OsLsi1 and OsLsi2 are located on chromosomes 2 and 3 respectively, mainly expressed in the roots; the gene OsLsi6 is located on chromosome 6, mainly expressed in the leaf sheaths and blades, and sparsely expressed in the roots (Ma et al., 2006; 2007; Yamaji et al., 200). The processe of the absorption and transportation of silicon in rice involves in 4 steps: in the first step, the silicic acid can be transported from the outer solution into the cells by the transport protein OsLsi1 in the exodermis, and the silicic acid is released into the apoplast of the aerenchyma by the transport protein OsLsi2; in the second step, the silicic acid is transported from the apoplast solution into the endodermis cells by the transport protein OsLsi1 in the endodermis, and the silicic acid is transported into the pericycles by the transport protein OsLsi2; in the third step, the silicon is transported from the pericycles to the above-ground part through the xylem vessel, in the non-polymeric monosilicic acid form, with the transpiration stream; in the fourth step, the transport protein OsLsi6 which is positioned in the xylem parenchyma cells close to the side of the vessels in the leaf sheaths and blades is responsible for unloading and distributing the silicon in the xylem, and dehydrated and polymerized under the transpiration effect, so as to form silica gel (SiO$_2$.nH$_2$O), which is deposited in the cell wall and the intercellular space in the different tissues and organs in the above-ground part, wherein more than 90% of silicon is present, in silica gel form, in rice.

Silicon is an important constituent element in rice body, and also a main constituent component in the cell wall of rice. After deposited in the apoplast (the cell wall and the intercellular space), silicon can not only reduce the cell voidage, but also can co-precipitate with cadmium and bind the same within the cell wall, so as to reduce the transportation of cadmium from the apoplast into the cell (Shi et al. 2005; Shi et al., 2010). Silicon can also improve the oxidative stress resistance in rice, alleviate the cadmium stress toxicity, and promote the increase of biomass (Liang et al., 2007), so that the exogenous application of silicon can improve the biomass of rice, and simultaneously reduce the cadmium content in the grains.

On the basis of the above mechanism of silicon, it is clear that silicon can prevent the accumulation of cadmium in the grains, so that silicon is determined to be used as a main exogenous regulator for preventing cadmium in rice grains. The above four authorized patents are the technologies for preventing the accumulation of cadmium in rice grains using the silica sol as the exogenous regulator, and provide the processes for preparing the silica sol, the rare-earth composite silica sol, the selenium dioxide composite silica sol.

However, the above four patents do not involve in how the silicon and selenium affect the active expression of the cadmium absorption and transportation-related gene in rice, how the foliage blocking agents are applied to achieve the precise regulation of the active expression of the cadmium absorption and transportation-related genes in rice, so as to inhibit the accumulation of cadmium in rice. These patents have not provided the precise regulation technologies and methods on these aspects yet.

CONTENTS OF THE INVENTION

In order to overcome the disadvantages and deficiencies in the prior art, the primary object of the present invention is to provide a method for preparing a foliage blocking agent for precise regulation of the expression of the cadmium absorption and transportation-related gene in rice.

Another object of the present invention is to provide a foliage blocking agent prepared by the above method.

Yet another object of the present invention is to provide a selenium composite silica sol foliage blocking agent for precise regulation of the expression of the cadmium absorption and transportation-related gene in rice.

The fourth object of the present invention is to provide the application of the above foliage blocking agent and/or selenium composite silica sol foliage blocking agent.

The fifth object of the present invention is to provide a foliage blocking method for precise regulation of the expression of the cadmium absorption and transportation-related gene in rice, which can precisely regulate the transportation of cadmium from the rice blades into the grains.

The objects of the present invention are achieved by the following technical solutions.

A method for preparing a foliage blocking agent for precise regulation of the expression of the cadmium absorption and transportation-related gene in rice, comprises the steps of (1) preparation of nano-sized selenium gel: an ascorbic acid solution is added to a selenium-containing solution in a water bath at 25~50° C., reacted for 2~5 h, separated the products, and purified, so as to obtain a nano-sized selenium gel;

(2) dispergation of the nano-sized selenium gel: an emulsifying agent is added to the nano-sized selenium gel prepared in step (1) under stirring, adjusted the pH to 4.5~6.5; so as to obtain a foliage blocking agent for precise regulation of the expression of the cadmium absorption and transportation-related gene in rice;

wherein, the selenium-containing compound in the selenium-containing solution in step (1) is preferably at least one from selenious acid, sodium selenite and potassium selenite;

the selenium content in the selenium-containing solution in step (1) is preferably 0.1~5% by mass, more preferably 0.5~1.5% by mass;

the ascorbic acid content in the ascorbic acid solution in step (1) is preferably 0.5~10% by mass, more preferably 1~3% by mass;

the molar ratio between the ascorbic acid in the ascorbic acid solution and the selenium in the selenium-containing solution in step (1) is (1:1)~(1:3);

the separation of the product in step (1) is preferably carried out by centrifugation;

the centrifugation is preferably carried out at a centrifugal force of 4000~10000 g, for 10~40 min;

the purification in step (1) is preferably carried out by washing the product with water and precipitating 2-5 times;

the final emulsifying agent content in step (2) is preferably 0.05~5% by mass;

the emulsifying agent in step (2) is preferably at least one from polyvinylpyrrolidone, polyvinyl alcohol, Tween series, and Span series;

the selenium content in the foliage blocking agent in step (2) is 0.15~2% by mass.

A foliage blocking agent for precise regulation of the expression of the cadmium absorption and transportation-related gene in rice is prepared by the above method.

A selenium composite silica sol foliage blocking agent for precise regulation of the expression of the cadmium absorption and transportation-related gene in rice, comprises the above foliage blocking agent and a silica sol.

A method for preparing the selenium composite silica sol foliage blocking agent for precise regulation of the expression of the cadmium absorption and transportation-related gene in rice, comprises the steps of:

the above foliage blocking agent and a silica sol are mixed to uniform, so as to obtain a selenium composite silica sol foliage blocking agent for precise regulation of the expression of the cadmium absorption and transportation-related gene in rice;

the foliage blocking agent and the silica sol have a volume ratio of (1:1)~(1:4);

the silica content in the selenium composite silica sol foliage blocking agent is 3~10% by mass;

the mass ratio between the selenium and the silica in the selenium composite silica sol foliage blocking agent is (1:10)~(1:55);

the silica sol is preferably an acidic silica sol;

the acidic silica sol has a pH of 4.5~6.5, and a silica content of 15%~20% by mass.

A method for preparing the acidic silica sol comprises the steps of:

a metallic silicon powder or a metal silicate are slowly added to an alkaline solution in a water bath at 40~60° C., under a stirring speed of 0.5~5 m/s, so as to obtain an alkaline silicon-containing solution; the alkaline silicon-containing solution is passed through a hydrogen-type weak acid cation exchange resin column at a speed of 1~10 mL/min, controlled the pH of the collection liquid at the column outlet to 4.5~6.5, so as to obtain an active acidic silica sol precursor; the active acidic silica sol precursor is heated to 40~60° C. in a microwaver or water bath, and maintained the temperature, stirred for 10~30 min, then stood, cooled, and aged for 30~60 min, so as to prepare the acidic silica sol;

the metal silicate is $Na_2SiO_3$, $K_2SiO_3$ or $Li_2SiO_3$, preferably $Na_2SiO_3$;

the alkaline silicon-containing solution has a concentration of 5% by mass to saturation, and a pH of 10~13;

the metallic silicon powder or the metal silicate requires a low impurity content;

the alkaline solution is sodium hydroxide solution, potassium hydroxide solution or aqueous ammonia, preferably aqueous ammonia;

the alkaline solution has a concentration of 0.1~5 M, preferably 0.2~2 M.

A selenium composite silica sol foliage blocking agent is prepared by the above method.

The application of the foliage blocking agent and/or the selenium composite silica sol foliage blocking agent in the technical filed for preventing heavy metal in plant.

A foliage blocking method for precise regulation of the expression of the cadmium absorption and transportation-related gene in rice, comprises the steps of:

the above foliage blocking agent, silica sol or selenium composite silica sol foliage blocking agent are diluted with water, in the period from the rice tillering stage to the jointing stage or from the heading stage to the filling stage, atomized and sprayed on the rice leaf blades once, or sprayed once for each period; the spraying is carried out in a sunny day or at 4~6 p.m. in a cloudy day;

the selenium content in the diluted foliage blocking agent is controlled at 0.01% to 0.1% by mass, preferably 0.05% by mass;

the silica content in the diluted silica sol or selenium composite silica sol foliage blocking agent is controlled at 0.1% to 0.1% by mass, preferably 0.5% by mass;

the spraying dosage in the period from the tillering stage to the jointing stage is 80~120 liters of the diluted foliage blocking agent, silica sol, or selenium composite silica sol foliage blocking agent per mu;

the spraying dosage in the period from the heading stage to the filling stage is 100~150 liters of the diluted foliage blocking agent, silica sol, or selenium composite silica sol foliage blocking agent per mu;

the atomization and spraying are preferably carried out as follows: the atomized droplets are controlled to have a particle size of less than 1000 microns, uniformly sprayed on both the front and the back surfaces of the rice blade.

The principles of the invention are as follows:

On the basis of the transport mechanism of the beneficial elements, such as silicon, selenium, and the like, in rice, and the transport mechanism of the heavy metal cadmium in rice, starting from these aspects, such as regulation of the distribution between the stems and the leaves, regulation of the activity of the transport protein, competition for the transportation channel, and the like, the key genes for controlling the transportation of cadmium from the rice blade into the grains, comprising OsLsi1, OsLsi2, OsHMA3, OsNramp5 and OsLCT1, are analyzed. The silica sol, selenium sol and selenium composite silica sol foliage blocking agents are developed, all of them can efficiently and precisely regulate the activity of the above key genes; as compared with those of spraying clean water, spraying the above sol materials on the leaf blades can efficiently reduce the cadmium content in rice. Secondly, the expression data analysis on the cadmium/silicon/selenium-related transport proteins queried and extracted from GenBank and RiceXPro databases show that the key step for the accumulation of cadmium in the rice grains lies in transportation of cadmium from the phloem to the grains. At present, it is found that the transport protein in the phloem related to the accumulation of cadmium in the rice grains is mainly OsLCT1. On the basis of the expression pattern analysis of bioinformatics, it is found that the gene OSLCT1 in the *Oryza. Sativa* L. spp. *japonica* is mainly expressed on the leaf blades, sparsely expressed in roots; in addition, the gene OSLCT1 not only shows different expressions in the different growth periods, wherein, during the transformation from the vegetative growth phase to the reproductive growth stage (tillering stage-heading stage), the expression level is significantly increased, and reached the maximum in the maturation stage; but also show a certain periodicity in its expression per day, wherein the expression level is significantly increased at 4~6 p.m. per day, and reached the maximum at 8~10 p.m., and the expression level is low in the rest period. The optimal technology for applying the above blocking agent materials is determined on the basis of the temporal and spatial specific expression patterns and the temporal and spatial expression specificity of various transport proteins in above analysis, so as to achieve the precise prevention of the transportation of cadmium from the rice blade to the grains.

As compared with the prior art, the present invention has the advantages and effects as follows:

(1) The present invention provides a foliage blocking method for precise regulation of the expression of the cadmium absorption and transportation-related gene in rice, wherein the activity of the cadmium absorption and transportation-related gene in rice is precisely regulated to inhibit the accumulation of cadmium in rice. As the physiological mechanism of high efficient blocking of the cadmium accumulation in rice by spraying the materials, such as selenium, silicon and the like on the leaf blades can be explained from the technical principles, and the field application of the blocking materials can be taught from the present invention, the foliage blocking method determined by the temporal and spatial expression data analysis on the cadmium/silicon/selenium-related transport genes in the present invention can efficiently inhibit the accumulation of cadmium in rice.

(2) The object of the present invention is to make the safety of the cadmium content in rice and the safety of the cadmium contaminated rice field meet the standards. It is hard to remove the selenium in soil in the large area of the cadmium contaminated rice field by using the processing methods, such as physical removal, chemical leaching, and the like. Starting from the basic theories, such as the mechanisms of transportation of the beneficial elements, such as silicon, selenium and the like, and the heavy metal cadmium, in rice, the present invention provides applicable key products, such as foliage blocking agent (selenium sol) and selenium composite silica sol foliage blocking agent as well as application methods thereof, in order to reduce the transportation of cadmium from the rice blades to the grains, thus increasing the safety of the rice. This control technology is one that is suitable for the low-to-moderate cadmium contaminated rice fields in China, which can provide technical supports for treating the large area of the cadmium contaminated rice fields in China.

(3) The present invention provides a selenium sol and a selenium composite silica sol foliage blocking agent, as well as a foliage blocking method, which has the characteristics, such as low cost and high efficiency.

(4) The present invention provides the products, such as silica sol, selenium sol foliage blocking agent, and selenium composite silica sol foliage blocking agent, the cost for spraying these blocking agents on the leaf blades is only 500~1500 yuan/hectare, which is 10% of that of applying the soil passivating agent, and has an equivalent or even better effect in reducing the cadmium content in rice.

PARTICULAR EMBODIMENTS

The present invention will be further described in details below in combination with the examples and accompanying drawings, but the embodiments of the present invention are not limited thereto.

Method for culturing the suspension cell of rice (*Oryza sativa* L. *Japonica*) comprises the steps of: the matured and plump seeds of *Oryza sativa* L. *Japonica* were selected, and sterilized with 70% by volume of alcohol or 30% by mass of sodium hypochlorite; uniformly spread the seeds on the plates containing a solid culture medium with forceps, cultured in an incubator, in dark, at a culture temperature of 25° C., for a period of time, then taken out the hypocotyls with forceps, cultured on another solid culture medium, so as to obtain callus tissues. 10 g of the callus tissues were broken, added to the conical flasks containing a liquid culture medium (50 mL), cultured in a shaker at a temperature of 28° C., for about 1 month, so as to obtain the suspension cells of the rice.

Figure 1:
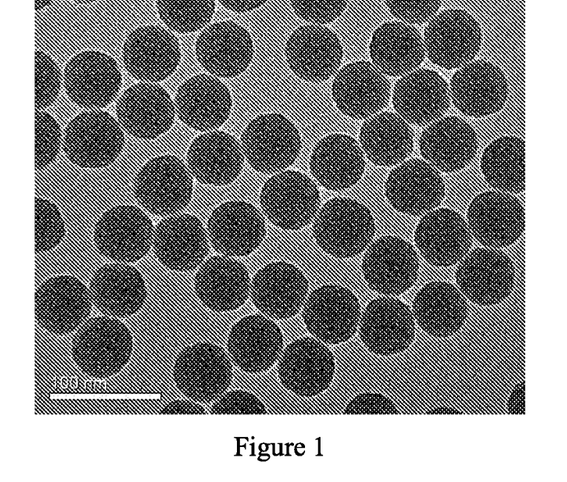
FIG. 1 is a transmission electron microscopic image of an acidic silica sol.

Example 1. Preparation of Acidic Silica Sol (1). 200 mL water was metered, and added 0.8 g of sodium hydroxide, so as to formulate 0.1 M sodium hydroxide solution; actuated a stirrer up to a speed of 0.5 m/s, and heated to 40° C., then slowly added 116 g $Na_2SiO_3$, fully dissolved, then cooled to the room temperature, so as to formulate an alkaline silicon solution with a pH of 10; passed the alkaline silicon solution through 100 mL (wet volume) hydrogen-type weak acid cation resin exchange column at an uniform speed of 1 mL/min, and controlled the pH value of the collection liquid at the column outlet to 4.5, so as to obtain an active acidic silica sol precursor; stirred the active acidic silica sol precursor in a water bath and heated to 40° C., maintained the temperature and stirred for 30 minutes, stood, cooled and aged for 60 min, so as to obtain an acidic silica sol, for use; the acidic silica sol having a pH of 4.5, and a silica content of 18% by mass;

(2) 200 mL water was metered, added 56 g potassium hydroxide, so as to formulate 5 M potassium hydroxide solution; actuated a stirrer up to a speed of 5 m/s, and heated to 60° C., then slowly added 110 g $Li_2SiO_3$, fully dissolved, then cooled to the room temperature, so as to prepare an alkaline silica solution with a pH of 12.5; passed the alkaline silica solution through 100 mL (wet volume) hydrogen-type weak acid cation resin exchange column at an uniform speed of 10 mL/min, and controlled the pH of the collection liquid at the column outlet to 6.5, so as to obtain an active acidic silica sol precursor; stirred the active acidic silica sol precursor in a water bath and heated to 60° C., maintained the temperature and stirred for 10 min, stood, cooled and aged for 30 min, so as to obtain an acidic silica sol, for use; the acidic silica sol having a pH of 6.5, and a silica content of 20% by mass;

(3) 200 mL water was metered, added 7 g aqueous ammonia, so as to formulate 1M ammonium hydroxide solution; actuated a stirrer up to a speed of 2 m/s and heated to 45° C., then slowly added 90 g $Na_2SiO_3$, fully dissolved, then cooled to the room temperature, so as to prepare an alkaline silica solution with a pH of 11; passed the alkaline silica solution through 100 mL (wet volume) hydrogen-type weak acid cation resin exchange column at an uniform speed of 5 mL/min, controlled the pH value of the collection liquid at the column outlet to 5.5, so as to obtain an active acidic silica sol precursor; stirred the active acidic silica sol precursor in a water bath and heated to 45° C., maintained the temperature and stirred for 20 min, stood, cooled and aged for 45 min, so as to obtain an acidic silica sol, for use; the acidic silica sol having a pH of 5.5, and a silica content of 15% by mass, with a TEM image shown in FIG. 1.

Example 2. Preparation of Selenium Sol Foliage Blocking Agent (1) a selenious acid solution was formulated, and controlled the selenium content at 0.1% by mass;

(2) 0.5% by mass of the ascorbic acid solution was added into the selenious acid solution prepared in step (1) in a water bath at 25° C., controlled the molar ratio between ascorbic acid and selenium to 1:1, and reacted for 2 h; then centrifuged in a centrifuge at 10000 g, for 10 min; followed by washing the precipitates three times with ultra-pure water, so as to obtain a nano-sized selenium gel;

(3) the emulsifying agent, polyvinylpyrrolidone, was added to the nano-sized selenium gel prepared in step (2), under stirring, wherein the final emulsifying agent content was 0.05% by mass, and adjusted the pH to 4.5, so as to obtain a foliage blocking agent (selenium sol foliage blocking agent) for precise regulation of the expression of the cadmium absorption and transportation-related gene in rice, wherein the selenium sol foliage blocking agent had a selenium content of 0.15% by mass.

Example 3. Preparation of Selenium Sol Foliage Blocking Agent (1) a sodium selenite solution was prepared, and controlled the selenium content at 5% by mass;

(2) 10% by mass of the ascorbic acid solution was added to the sodium selenite solution prepared in step (1) in a water bath at 50° C., controlled the molar ratio between ascorbic acid and selenium to 1:3, and reacted for 5 h; then centrifuged in a centrifuge at 4000 g for 40 min, followed by washing the precipitates 3 times with ultra-pure water, so as to obtain a nano-sized selenium gel;

(3) an emulsifying agent, Span-80, was added to the nano-sized selenium gel prepared in step (2), under stirring, wherein the final emulsifying agent content was 5% by mass, and adjusted the pH to 6.5, so as to obtain a foliage blocking agent (selenium sol foliage blocking agent) for precise regulation of the expression of the cadmium absorption and transportation-related gene in rice, wherein the selenium sol foliage blocking agent had a selenium content of 2% by mass.

Example 4. Preparation of Selenium Sol Foliage Blocking Agent (1) a potassium selenite solution was formulated, and controlled the selenium content at 1.5% by mass;

(2) 2.5% by mass of the ascorbic acid solution was added to the potassium selenite solution prepared in step (1) in a water bath at 50° C., controlled the molar ratio between ascorbic acid and selenium to 1:1.5, and reacted for 3 h; then centrifuged in a centrifuge at 5000 g for 30 min, followed by washing the precipitates 3 times with ultra-pure water, so as to obtain a nano-sized selenium gel;

(3) an emulsifying agent, Tween-80, was added to the nano-sized selenium gel prepared in step (2), under stirring, wherein the final emulsifying agent content was 1.5% by mass, and adjusted the pH to 5.5, so as to obtain a foliage blocking agent (selenium sol foliage blocking agent) for precise regulation of the expression of the cadmium absorption and transportation-related gene in rice, wherein the selenium sol foliage blocking agent had a selenium content of 1.5% by mass.

Figure 2:
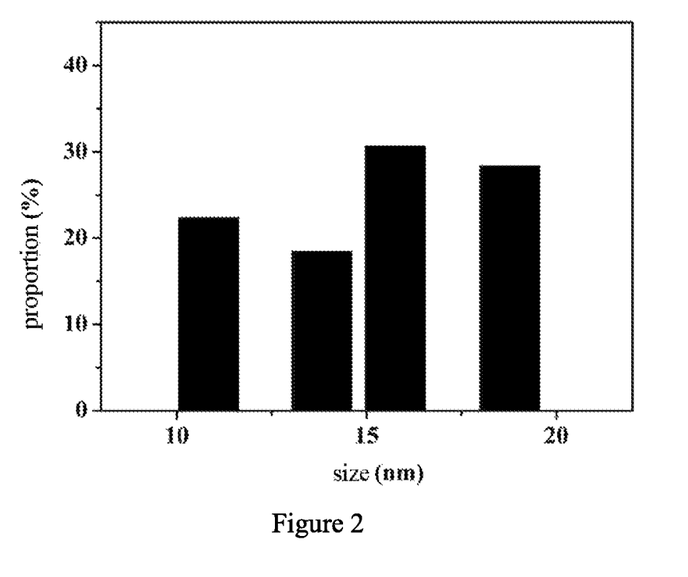
FIG. 2 is a diagram showing the particle size distribution of the foliage blocking agent (selenium sol).
Figure 3:
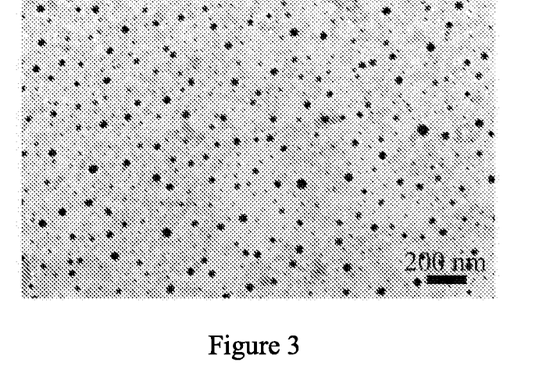
FIG. 3 is a transmission electron microscopic image of the foliage blocking agent (selenium sol).
Figure 4:
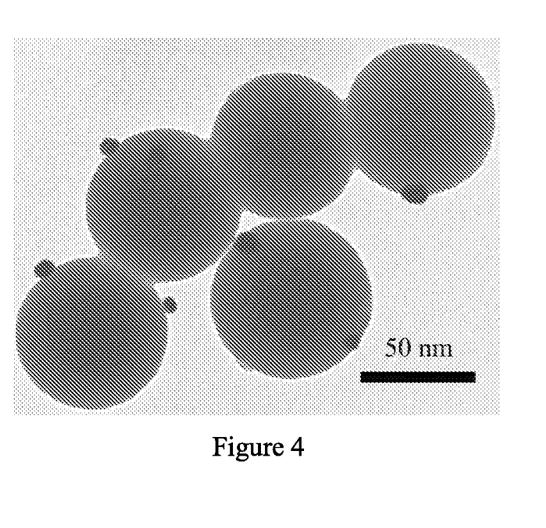
FIG. 4 is a transmission electron microscopic image of the selenium composite silica sol foliage blocking agent.
Figure 5:
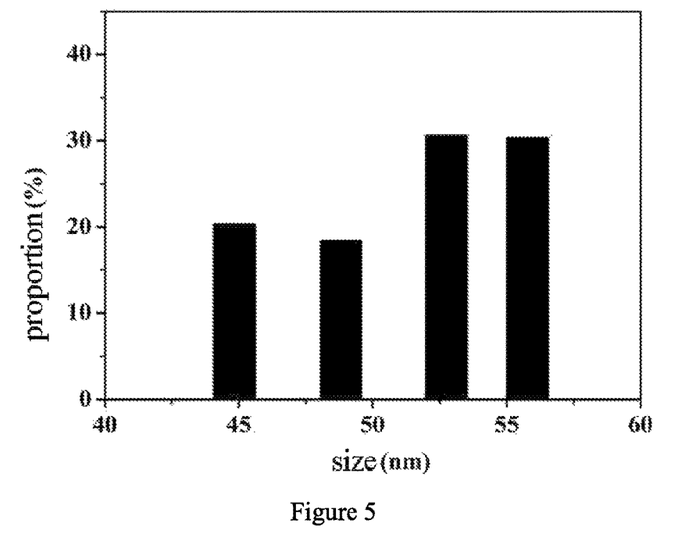
FIG. 5 is a diagram showing the particle size distribution of the selenium composite silica sol foliage blocking agent.

(4) the selenium sol foliage blocking agent samples prepared in step (3) were carried out a particle size distribution analysis, the results showed that the average particle diameter was 17.35±1.4 nm, as shown FIG. 2; the prepared selenium sol foliage blocking agent samples were carried out a morphology analysis by TEM, the nano-sized selenium formed in the reaction system was a spherical particle, and uniformly dispersed, having an average particle diameter of about 15 nm, as shown in FIG. 3.

Example 5. Preparation of Selenium Composite Silica Sol Foliage Blocking Agent

The selenium sol foliage blocking agent prepared in example 4 was mixed with the acidic silica sol, having a pH of 5.5, and silica content of 15% by mass, the acidic silica sol, having a pH of 4.5, and silica content of 18% by mass, and the acidic silica sol, having a pH of 6.5, and silica content of 20% by mass, prepared in example 1, respectively, wherein the volume ratio between the selenium sol foliage blocking agent and the silica sol was 1:1, 1:2 and 1:4 respectively, stirred for 30 min, so as to obtain a selenium composite silica sol foliage blocking agent for precise regulation of the expression of the cadmium absorption and transportation-related gene in rice; the silica content in the prepared selenium composite silica sol foliage blocking agent was 7.5%, 6% and 4% by mass respectively, and the mass ratio between the selenium and silica were 1:10, 1:24 and 1:53 respectively. The prepared selenium composite silica sol foliage blocking agent samples having a silica content of 7.5% by mass were carried out a morphology analysis by TEM, as shown in FIG. 4, the nano-sized selenium formed in the reaction system was loaded on the surface of the nano-sized silica sphere, having a particle size of 45~55 nm (FIG. 5).

Example 6. Precise Regulation of the Acidic Silica Sol on the Expression of the Cadmium Transport Gene in Rice Suspension Cell and Inhibition of the Same on the Cadmium Absorption The silica sol prepared in example 1 having a pH of 5.5 and a silica content of 15% by mass, was diluted to a silica content of 0.5% by mass, and used to treat the rice cells (*Oryza sativa* L. *Japonica*) for 24 h, then added various concentrations of cadmium, and continued to culture for 24 h, then extracted the RNA of the rice suspension cells, and carried out qRT-PCR analysis (the corresponding primers shown in table 14). The results showed that as compared with the blank control (CK, without addition of silica sol), at the same cadmium concentration, after treating with the silica sol, the expression levels of the genes OsLsi1, OsNramp5 and OsLCT1 in the rice cells were significantly reduced (table 1, table 2, table 3), and the expression level of the gene OsHMA3 was significantly increased (table 4). The proteins expressed by the genes OsLsi1 and OsNramp5 may be associated with the absorption of cadmium, the proteins expressed by the gene OsLsi1 may be associated with the transportation of cadmium from the phloem to the grains, the down-regulations of the expression of the three genes facilitated the reduction of the absorption of cadmium in rice and the reduction of the transportation of cadmium into the grains; and the protein expressed by gene OsHMA3 may have the functionality which was associated with the transportation of cadmium into the vacuoles, so as to reduce the transportation of the same into the xylem, and in turn reduce the transportation of cadmium from the roots to the above-ground part. After the silica sol was used to precisely regulate the above genes, the cadmium accumulation levels in the rice cells were significantly reduced, as compared with the controls, after treating with silica sols at 10, 20, 40 μM Cd, the cadmium concentrations in the rice cells were reduced by 72.8%, 75.5% and 81.3% respectively (table 5).

TABLE 1

The effects of the silica sol treatment on the expression levels of the transport gene OsLsi1 in the rice suspension cells

|  | Blank (CK) | Silica sol treatment | Average reduction as compared with the control (%) |
| --- | --- | --- | --- |
| 0 | 4.13 ± 0.81 | 3.66 ± 0.75 | 11.4 |
| Cd (10 μM) | 15.62 ± 1.32 | 13.25 ± 0.92 | 15.2 |
| Cd (20 μM) | 19.85 ± 1.25 | 16.43 ± 0.75 | 17.2 |
| Cd (40 μM) | 22.78 ± 0.97 | 17.65 ± 0.84 | 22.5 |

TABLE 2

The effects of the silica sol treatment on the expression levels of the cadmium transport gene OsNramp5 in the rice suspension cells

|  | Blank (CK) | Silica sol treatment | Average reduction as compared with the control (%) |
| --- | --- | --- | --- |
| 0 | 2.8 ± 0.25 | 1.9 ± 0.36 | 32.1 |
| Cd (10 μM) | 4.2 ± 0.32 | 3.5 ± 0.29 | 16.7 |
| Cd (20 μM) | 5.6 ± 0.28 | 4.1 ± 0.35 | 26.8 |
| Cd (40 μM) | 6.8 ± 0.45 | 4.6 ± 0.42 | 32.4 |

TABLE 3

The effects of the silica sol treatment on the expression levels of the cadmium transport gene OsLCT1 in rice suspension cells.

|  | Blank (CK) | Silica sol treatment | Average reduction as compared with the control (%) |
| --- | --- | --- | --- |
| 0 | 1.85 ± 0.09 | 1.43 ± 0.06 | 22.7 |
| Cd (10 μM) | 1.52 ± 0.04 | 0.71 ± 0.07 | 53.3 |
| Cd (20 μM) | 1.44 ± 0.04 | 0.58 ± 0.05 | 59.7 |
| Cd (40 μM) | 1.32 ± 0.06 | 0.67 ± 0.08 | 49.2 |

TABLE 4

The effects of the silica sol treatment on the expression levels of the cadmium transport gene OsHMA3 in rice suspension cells

|  | Blank (CK) | Silica sol treatment | Average increase as compared with the control (%) |
| --- | --- | --- | --- |
| 0 | 2.25 ± 0.15 | 3.11 ± 0.32 | 38.2 |
| Cd (10 μM) | 1.84 ± 0.18 | 3.07 ± 0.21 | 66.8 |
| Cd (20 μM) | 2.66 ± 0.21 | 3.26 ± 0.3 | 22.6 |
| Cd (40 μM) | 3.05 ± 0.26 | 3.64 ± 0.31 | 19.3 |

TABLE 5

The effects of the silica sol treatment on the cadmium contents in the rice cells (μg kg$^{-1}$)

|  | Blank (CK) | Silica sol treatment | Average reduction as compared with the control (%) |
| --- | --- | --- | --- |
| Cd (10 μM) | 9.2 ± 0.8 | 2.5 ± 0.6 | 72.8 |
| Cd (20 μM) | 18.4 ± 1.1 | 4.5 ± 0.7 | 75.5 |
| Cd (40 μM) | 36.4 ± 6.8 | 6.8 ± 0.9 | 81.3 |

Example 7. Precise Regulation of the Selenium Sol Foliage Blocking Agent on the Expression of the Cadmium Transport Gene in the Rice Suspension Cells and Inhibition of the Same on the Cadmium Absorption The selenium sol foliage blocking agents prepared in example 4 were diluted to various concentrations respectively (0.01%, 0.05%, 0.1%), and cultured the rice suspension cells (*Oryza sativa* L. *Japonica*) for 24 h, then added various concentrations of cadmium (10 μM, 20 μM and 40 μM), and cultured for 24 h, extracted the RNA from the rice cells, and carried out reverse transcription, then detected the expression levels of the genes OsNramp5 and OsHMA3 (the corresponding primers shown in table 14). The results showed that (table 6, table 7), as compared with the blank (CK, without addition of selenium sol foliage blocking agent), the expression levels of the gene OsHMA3 in the rice suspension cells were up-regulated in duplications, and the expression levels of the gene OsNramp5 in the rice suspension cells were significantly suppressed; at high cadmium concentration (40 μM), after treating with 0.05% selenium sol foliage blocking agent, the suppression effects on the expression of the gene OsNramp5 were optimal. The protein expressed by the gene OsNramp5 may be associated with the absorption of cadmium, and the protein expressed by the gene OsHMA3 may have the functionality which may be associated with the transportation of cadmium into the vacuoles, so as to reduce the transportation of the same into the xylem, and in turn reduce the transportation of cadmium from the roots to the above-ground part. After the selenium sol foliage blocking agent was used to precisely regulate the above genes, the cadmium accumulation levels in the rice cells were significantly reduced, and as compared with the control, at 10, 20, 40 μM Cd, after treating with 0.05% selenium sol foliage blocking agent, the cadmium concentrations in the rice cells were reduced by 47.1%, 55.3% and 61.7% respectively (table 8).

TABLE 6

The effects of the selenium sol foliage blocking agent on the expression levels of the cadmium transport protein OsNramp5 in the rice suspension cells.

|  | Blank (CK) | Selenium (0.01%) | Selenium (0.05%) | Selenium (0.1%) |
| --- | --- | --- | --- | --- |
| 0 | 2.11 ± 0.15 | 1.82 ± 0.04 | 1.97 ± 0.08 | 1.76 ± 0.09 |
| Cd (10 μM) | 4.23 ± 0.28 | 1.96 ± 0.09 | 1.34 ± 0.06 | 0.84 ± 0.04 |
| Cd (20 μM) | 6.72 ± 0.05 | 1.55 ± 0.08 | 0.92 ± 0.07 | 0.63 ± 0.04 |
| Cd (40 μM) | 7.96 ± 0.08 | 1.34 ± 0.05 | 0.85 ± 0.08 | 1.55 ± 0.06 |

TABLE 7

The effects of the selenium sol foliage blocking agent on the expression levels of the cadmium transport protein OsHMA3 in the rice suspension cells

|  | Blank (CK) | Selenium (0.01%) | Selenium (0.05%) | Selenium (0.1%) |
| --- | --- | --- | --- | --- |
| 0 | 1.21 ± 0.15 | 1.56 ± 0.18 | 1.85 ± 0.18 | 2.54 ± 0.21 |
| Cd (10 μM) | 1.86 ± 0.32 | 2.25 ± 0.28 | 3.14 ± 0.29 | 3.81 ± 0.26 |
| Cd (20 μM) | 2.26 ± 0.25 | 2.81 ± 0.28 | 3.62 ± 0.28 | 4.97 ± 0.28 |
| Cd (40 μM) | 2.45 ± 0.31 | 3.26 ± 0.31 | 3.87 ± 0.24 | 4.52 ± 0.24 |

TABLE 8

The effects of 0.05% selenium sol foliage blocking agent treatment on the cadmium contents in the rice cells (μg kg$^{-1}$).

|  | Blank (CK) | Selenium (0.05%) | Average reduction as compared with the control (%) |
|---|---|---|---|
| Cd (10 μM) | 8.7 ± 0.5 | 4.6 ± 0.4 | 47.1 |
| Cd (20 μM) | 15.2 ± 0.9 | 6.8 ± 0.7 | 55.3 |
| Cd (40 μM) | 29.8 ± 3.2 | 11.4 ± 1.2 | 61.7 |

TABLE 10

The effects of various foliage blocking materials on the cadmium accumulation levels in the rice stems and leaves

|  | Cadmium level (mg/kg) | Reduction as compared with control (%) |
|---|---|---|
| CK | 3.45 ± 0.47 |  |
| Silica sol | 1.25 ± 0.11 | 63.8 |
| Selenium sol | 1.67 ± 0.27 | 51.6 |
| Selenium composite silica sol | 1.17 ± 0.09 | 66.1 |

Example 8. Precise Regulation of the Selenium Sol Foliage Blocking Agent, Silica Sol, and Selenium Composite Silica Sol Foliage Blocking Agent on the Expression of the Cadmium Transport Gene in Rice and Inhibition of the Same on the Cadmium Absorption Under Pot Culture Conditions The rice (a variety of YouYou 128) was cultured in Kimura culture medium for 3 weeks, then transferred into a culture solution containing 5 μM Cd, and carried out the following treatments: (1) treatments with control (CK): 200 mL deionized water was sprayed on each pot; (2) treatments by spraying the silica sol foliage blocking agent on the leaf blades: 200 mL the diluted silica sol (the silica sol prepared in example 1, having a pH of 5.5 and a silica content of 15% by mass, then diluted to a silica content of 0.5% by mass) was sprayed on each pot; (3) treatments by spraying the selenium sol foliage blocking agent on the leaf blades: 200 mL the diluted selenium sol foliage blocking agent (prepared in example, then diluted to a selenium content of 0.05%) was sprayed on each pot; (4) treatments by spraying the selenium composite silica sol foliage blocking agent on the leaf blades: 200 mL the selenium composite silica sol foliage blocking agent was sprayed on each pot (prepared in example 5, then diluted to a silica content of 0.5% and a selenium content of 0.05%). After one week, the samples were collected, and tested the relative expression levels of the genes OsLsi1 and OsLsi2 in the roots (corresponding primers shown in table 14), and tested the cadmium contents in the stems and leaves. The results showed that all of the three sol foliage blocking agents can precisely inhibit the relative expression levels of the genes OsLsi1 and OsLsi2 (table 9), so as to reduce the cadmium contents in the rice stems and leaves. As compared with the control, after the treatments by spraying the silica sol, selenium sol and selenium composite silica sol on leaf blades, the cadmium accumulation levels in the above-ground part of rice were reduced by 63.8%, 51.6%, 66.1% respectively; and the selenium composite silica sol had the optimal effects in inhibiting the cadmium accumulation in the above-ground part of rice (table 10).

Example 9. The Effects of the Selenium Sol Foliage Blocking Agent, Silica Sol and Selenium Composite Silica Sol Foliage Blocking Agents on the Reduction of the Cadmium Accumulation in the Rice Grains in the Field Conditions The test time was from April to November, 2014, the test site was located in a Cd contaminated rice field in Hongxing village, Dongtang town, Renhua county, Shaoguan city, Guangdong province, China. The surface soils were collected from this plot (0~30 cm) for analysis. The soils had a pH of about 5.86, a Cd content of about 1.85 mg kg$^{-1}$, and an As content of 18.20 mg kg$^{-1}$. This plot was a typical cadmium contaminated rice field resulting from mining. The rices to be tested were the early mature variety of WuYou 613 in 2014, and the late mature variety of WuFengYou 615.

Four treatments were set for the tests as follows: (1) a blank control, (CK), i.e., spraying an equal amount of clean water; (2) spraying the silica sol foliage blocking agent (prepared in example 1, having a pH of 5.5 and a silica content of 15% by mass) on the leaf blades; (3) spraying the selenium sol foliage blocking agent (prepared in example 4) on the leaf blades; (4) spraying the selenium composite silica sol foliage blocking agent (prepared in example 5) on the leaf blades. Each treatment was repeated 3 times, arranged in random, tested 12 plots in total, wherein each plot had an area of 5*64=30 m$^2$, and was ensured to be separately irrigated and drained.

Spraying Technology:

In the early mature rices, the blocking agents were sprayed twice for each of the treatments, once during the period from the tillering stage to the jointing stage, the other once during the period from the heading stage to the filling stage. During the period from the tillering stage to the jointing stage, the sprayed silica sol had a silica content of 0.1%, the selenium sol had a selenium content of 0.01%, and the selenium composite silica sol had a silica content of 0.1% (prepared in example 5, having a silica content of 7.5% by mass, a mass ratio between silica and selenium of 10:1), and during the period from heading stage to the filling stage, the sprayed silica sol had a silica content of 0.5%, and the selenium sol had a selenium content of 0.05%, the selenium

TABLE 9

The effects of various foliage blocking materials on the relative expression levels of the genes OsLsi1 and OsLsi2 in the rice roots

|  |  | OsLsi1 | OsLsi2 |
|---|---|---|---|
| Control (CK) | Relative expression level | 1 ± 0.0282 | 1 ± 0.1263 |
| Silica sol | Relative expression level | 0.485 ± 0.118 | 0.629 ± 0.125 |
|  | Reduction as compared with control (%) | 51.45 | 37.07 |
| Selenium sol | Relative expression level | 0.486 ± 0.103 | 0.326 ± 0.030 |
|  | Reduction as compared with control (%) | 51.39 | 67.4 |
| Selenium composite silica sol | Relative expression level | 0.451 ± 0.078 | 0.314 ± 0.078 |
|  | Reduction as compared with control (%) | 54.86 | 68.53 | composite silica sol had a silica content of 0.5% (prepared in example 5, having a silica content of 7.5% by mass, and a mass ratio between silica and selenium of 10:1). During the period from the tillering stage to the jointing stage, the spraying dosage for each of the blocking agents was 100 liters/mu, the spraying was carried out at 4:00 p.m. in a sunny day; during the period from the heading stage to the filling stage, the spraying dosage of each of the blocking agents was 150 liters/mu, the spraying was carried out at 6:00 p.m. in a cloudy day. During spraying, the atomized droplets were controlled to have a particle size of less than 1000 microns, and uniformly sprayed on both the front and back surfaces of the rice blade.

In the late mature rice, the blocking agent was sprayed once for each of the treatments. The spraying was carried out during the period from the tillering stage to the jointing stage, and the sprayed silica sol had a silica content of 1%, the selenium sol had a selenium content of 0.1%, and the selenium composite silica sol had a silica content of 1% (prepared in example 5, having a silica content of 7.5% by mass, and a mass ratio between silica and selenium of 10:1); the spraying dosage for each of the blocking materials was 120 liters/mu, the spraying was carried out at 5:00 p.m. in a sunny day. During spraying, the atomized droplets were controlled to have a particle size of less than 1000 microns, and uniformly sprayed on both front and back surfaces of the rice blade.

As shown in tables 11-12, after the treatments by various of foliage blocking agents, both the early and late mature rices in 2014 had an increased yield; wherein the early mature rice had much more increase level than that of the late mature rice, and after the treatment with the selenium composite silica sol, both the early and late mature rices had a significant increase level in rice yield, which was increased by 7.32% and 4.85% respectively as compared with the control.

TABLE 11

The statistical results for the yields of the early mature rice in 2014

| | Plot yield (wet yield, kilogram) | | | Plot average yield | Dry field per mu | Yield increase |
|---|---|---|---|---|---|---|
| | I | II | III | (kilogram) | (kilogram) | (%) |
| control | 37 | 37.25 | 38.5 | 37.58a | 647.2 | |
| Silica sol | 38 | 39.25 | 40.25 | 39.17ab | 674.6 | 4.23 |
| Selenium sol | 38 | 40.2 | 39.5 | 39.23ab | 675.7 | 4.41 |
| Selenium composite silica sol | 40 | 41 | 40 | 40.33b | 694.6 | 7.32 |

TABLE 12

The statistical results for the yields of the late mature rice in 2014

| | Plot yield (wet yield, kilogram) | | | Plot average yield | Dry yield per mu | Yield increase |
|---|---|---|---|---|---|---|
| | I | II | III | (kilogram) | (kilogram) | (%) |
| Control | 33.5 | 34.5 | 33.5 | 33.83a | 585.5 | |
| Silica sol | 32.5 | 37.5 | 34 | 34.6a | 598.8 | 2.27 |
| Selenium sol | 33.7 | 34.7 | 35.1 | 34.5a | 597.1 | 1.98 |
| Selenium composite silica sol | 34 | 38 | 34.25 | 35.43b | 613.9 | 4.85 |

As shown in table 13, the treatments by spraying the foliage blocking agent can significantly reduce the cadmium content in rice. As compared with the control, after spraying the silica sol, selenium sol, and selenium composite silica sol foliage blocking agents, the cadmium contents in the early mature rices in 2014 were reduced by 64.3, 49.0 and 85.9% respectively, and the cadmium contents in the late mature rices were reduced by 34.2%, 28.8% and 46.4% respectively. Spraying the selenium composite silica sol foliage blocking agent had significantly better effects on the reduction of the cadmium content in rice over the silica sol and selenium sol foliage blocking agents; and spraying the foliage blocking agent twice during the rice growth phase had significantly better effects on reduction of the cadmium content in rice over solely spraying the same once. In the early mature rice in 2014, after spraying the selenium composite silica sol foliage blocking agent once for each of the periods from the tillering stage to the jointing stage, and from the heading stage to the filling stage, the cadmium content in rice can be reduced from 1.51 mg/kg in the control to 0.162 mg/kg, which had reached the Food Sanitation Standards. Therefore, the foliage blocking technology for precise regulation of the expression of the cadmium absorption and transportation-related gene in rice can achieve the safety of the rice production in the low-to-mediate contaminated rice field.

TABLE 13

The effects of various foliage blocking materials on the cadmium accumulation levels in rice

| | cadmium content in early mature rice | | Cadmium content in late mature rice | |
|---|---|---|---|---|
| | Cadmium content (mg/kg) | Reduction as compared with control (%) | Cadmium content (mg/kg) | Reduction as compared with control (%) |
| Control | 1.151 ± 0.074 | 0.0 | 1.283 ± 0.098 | 0.0 |
| Silica sol | 0.411 ± 0.006 | 64.3 | 0.844 ± 0.074 | 34.2 |
| Selenium sol | 0.587 ± 0.014 | 49.0 | 0.914 ± 0.076 | 28.8 |
| Selenium composite silica sol | 0.162 ± 0.049 | 85.9 | 0.688 ± 0.048 | 46.4 |

TABLE 14

The primers for identification of the cadmium, silicon and arsenic transportation-related genes in rice

| Gene name | Forward primer | Reverse primer |
|---|---|---|
| OsNramp5 | TGAGCTGCTCTGGGTGATTC | TGCCAGCAGCCATAGGAAAA |
| OsLCT1 | TGGCGATCTTTGGAGGCTTT | CGCCGAGGTCGATAAGAACA |

TABLE 14-continued

The primers for identification of the cadmium, silicon and arsenic transportation-related genes in rice

| Gene name | Forward primer | Reverse primer |
|---|---|---|
| OsHMA3 | AGAACAGCAGGTCGAAGACG | ATTGCTCAAGGCCATCTGCT |
| OSLsi1 | CGGTGGATGTGATCGGAACCA | CGTCGAACTTGTTGCTCGCCA |
| OSLsi2 | ATCTGGGACTTCATGGCCC | ACGTTTGATGCGAGGTTGG |

The above examples are the preferred embodiments in the present invention, but the embodiments of the present invention are not limited thereto. Any other changes, modifications, alternatives, combinations, simplifications, made without departing from the spirit and principles of the present invention, should be the equivalent replacement mode, and included in the scope of protection of the present invention.

The invention claimed is:

1. A selenium composite silica sol foliage blocking agent for precise regulation of the expression of the cadmium absorption and transportation-related gene in rice, comprising a foliage blocking agent and an acidic silica sol; wherein the foliage blocking agent is prepared by the method comprising the steps of:
(1) preparing a nano-sized selenium gel comprising adding an ascorbic acid solution into a selenium-containing solution in a water bath at 25-50° C., for 2-5 h, and separating and purifying products, so as to obtain a nano-sized selenium gel; and
(2) dispersing the nano-sized selenium gel comprising adding an emulsifying agent is added to the nano-sized selenium gel prepared in step (1) under stirring, and adjusting the pH to 4.5-6.5,
wherein the selenium composite silica sol foliage blocking agent for precise regulation of the expression of the cadmium absorption and transportation-related gene in rice is obtained.

2. The selenium composite silica sol foliage blocking agent of claim 1, wherein the selenium-containing solution in step (1) comprises at least one of seleninic acid, sodium selenite and potassium selenite.

3. The selenium composite silica sol foliage blocking agent of claim 1, wherein a molar ratio between the ascorbic acid and selenium in step (1) is (1:1)-(1:3).

4. The selenium composite silica sol foliage blocking agent of claim 1, wherein a final emulsifying agent content in step (2) is 0.05~5% by mass; and the foliage blocking agent in step (2) has a selenium content of 0.15~2% by mass.

5. The selenium composite silica sol foliage blocking agent of claim 1, wherein
the selenium composite silica sol foliage blocking agent has a silica content of 3~10% by mass; and
a mass ratio between selenium and the silica in the selenium composite silica sol foliage blocking agent is (1:10)-(1:55).

6. The selenium composite silica sol foliage blocking agent of claim 1, wherein
the acidic silica sol has a pH of 4.5-6.5, a silica content of 15%-20% by mass; and
the method for preparing the acidic silica sol, comprises the steps of:
adding a metallic silicon powder or a metal silicate to an alkaline solution in a water bath at 40-60° C., at a stirring speed of 0.5~5 m/s, so as to obtain an alkaline silicon-containing solution;
passing the alkaline silicon-containing solution through a hydrogen-type weak acid cation exchange resin column at a speed of 1~10 mL/min, and controlling the pH value of the collection liquid at the column outlet to 4.5~6.5, so as to obtain an active acidic silica sol precursor; and
heating the active acidic silica sol precursor to 40~60° C. in a microwaver or water bath, maintaining temperature and stirring for 10~30 min, then cooling for 30~60 min, so as to prepare the acidic silica sol.

7. A foliage blocking method for precise regulation of the expression of the cadmium absorption and transportation-related gene in rice, comprising the steps of:
diluting the selenium composite silica sol foliage blocking agent of claim 6 to obtain diluted selenium composite silica sol foliage blocking agent,
atomizing diluted selenium composite silica sol foliage blocking agent, and
spraying the diluted selenium composite silica sol foliage blocking agent once on the rice leaf blades during the period from the rice tillering stage to the jointing stage, or from the heading to the filling stage, or once for each period, wherein the spraying is carried out in a sunny day or at 4-6 p.m. on a cloudy day;
wherein silica content in the diluted selenium composite silica sol foliage blocking agent is controlled at 0.1%~0.1% by mass;
wherein a spraying dosage during the period from the tillering stage to the jointing stage is 80~120 liters of the diluted selenium composite silica sol foliage blocking agent per mu;
wherein a spraying dosage during the period from the heading stage to the filling stage is 100~150 liters of the diluted selenium composite silica sol foliage blocking agent per mu; and
wherein the silica sol is an acidic silica sol.

* * * * *